United States Patent
Quiroz et al.

(10) Patent No.: US 10,245,409 B2
(45) Date of Patent: Apr. 2, 2019

(54) PACKAGING AND ORGANIZING COILS OF MEDICAL TUBING

(71) Applicant: Fresenius Medical Care Holdings, Inc., Waltham, MA (US)

(72) Inventors: Erik A. Quiroz, Benicia, CA (US); Anina Cooter, San Francisco, CA (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 293 days.

(21) Appl. No.: 15/205,521

(22) Filed: Jul. 8, 2016

(65) Prior Publication Data
US 2018/0008798 A1   Jan. 11, 2018

(51) Int. Cl.
A61M 25/00 (2006.01)
A61M 1/14 (2006.01)
A61M 39/08 (2006.01)
A61M 1/36 (2006.01)

(52) U.S. Cl.
CPC ............ *A61M 25/002* (2013.01); *A61M 1/14* (2013.01); *A61M 1/367* (2013.01); *A61M 39/08* (2013.01); *A61M 2039/087* (2013.01); *A61M 2209/084* (2013.01)

(58) Field of Classification Search
CPC ...... A61M 25/002; A61M 39/08; H02G 3/32; B65D 85/04
See application file for complete search history.

(56) References Cited

U.S. PATENT DOCUMENTS

| | | | |
|---|---|---|---|
| 2,724,538 A * | 11/1955 | Schweich | B65D 5/2033 206/303 |
| 4,850,974 A | 7/1989 | Bickelhaupt et al. | |
| 5,167,463 A * | 12/1992 | Corbishley | B42F 13/10 402/13 |
| 5,197,597 A * | 3/1993 | Leary | A61B 17/06133 206/482 |
| 5,309,604 A | 5/1994 | Poulsen | |
| 5,344,011 A | 9/1994 | DiBernardo et al. | |
| 5,350,357 A * | 9/1994 | Kamen | A61M 1/28 604/29 |
| 6,196,503 B1 | 3/2001 | Cernosek et al. | |
| 7,461,741 B2 | 12/2008 | State et al. | |
| 8,177,736 B2 | 5/2012 | Kopperschmidt | |
| 2005/0194276 A1 * | 9/2005 | Lubs | A61M 25/002 206/364 |
| 2007/0149914 A1 | 6/2007 | Axelsson et al. | |
| 2010/0200706 A1 * | 8/2010 | Harding | A61M 5/1415 248/62 |

* cited by examiner

*Primary Examiner* — Nathan R Price
*Assistant Examiner* — Tasnim Mehjabin Ahmed
(74) *Attorney, Agent, or Firm* — Fish & Richardson P.C.

(57) ABSTRACT

A device and method for holding coils of medical tubing is provided to simplify packaging and organizing the various coils of medical tubing needed for a medical device. This will make it easier for the patient to manipulate each coil of tubing, particularly in a home setting involving a home dialysis machine operated by the patient. The tube holding device advantageously reduces the probability of entanglement and groups the coils of tubing individually. It also mitigates and/or eliminates the need for tape to bundle the coils. Specifically, benefits of the tube holding device according to the system described herein include: reduced cost; ease-of-use; prevention of entanglement of coils of tubing; ease of packaging and shipping; and does not require packaging tape to bundle tubing.

14 Claims, 9 Drawing Sheets

PACKAGING AND ORGANIZING COILS OF MEDICAL TUBING

TECHNICAL FIELD

This application relates generally to medical tubing for medical devices.

BACKGROUND

Dialysis is a treatment used to support a patient with insufficient renal function. The two principal dialysis methods are hemodialysis and peritoneal dialysis. During hemodialysis (HD), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis (PD), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

HD treatments are typically performed on a patient multiple times a week using an HD machine in a clinic or home environment with each treatment lasting a least a few hours. PD treatments are done several times a day on a patient, often at home and often performed overnight while a patient is asleep using an automated PD machine called a PD cycler. A PD cycler is designed to control the entire PD process so that it can be performed at home without clinical staff in attendance. Many PD cyclers are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle. Dialysis machines are typically equipped with interfaces for receiving inputs and providing information to users during treatments.

Tubing (which may also be referred to herein as a "line") for conveying fluid specifically for medical purposes, such as in HD and/or PD treatments, may be looped and packaged together, often with tape, in connection with shipping and/or organizing the tubing for installation at a dialysis machine. Particularly in connection with home dialysis treatments, the bundles of various tubing can be confusing and frustrating for a patient or user to handle because the loops of tubing are not individualized and separating the tubing from each other in connection with setup at a dialysis machine can often lead to entanglement of the tubing.

Accordingly, it would be desirable to provide a system and method for reducing the possibility of entanglement of medical tubing in connection with packaging, shipping and/or use.

SUMMARY

According to the system described herein, a device for holding medical tubing includes a semi-rigid sheet, a plurality of adjustable tabs disposed on the semi-rigid sheet, and a plurality of locking slits that receive the plurality of adjustable tabs to secure coils of medical tubing to the plastic sheet. The plurality of adjustable tabs and the plurality of locking slits are disposed on the semi-rigid sheet in at least one of: (i) a front and reverse configuration in which at least one of the plurality of adjustable tabs and at least one of the plurality of locking slits are disposed on a front side of the semi-rigid sheet, and at least another one of the plurality of adjustable tabs and at least another one of the plurality of locking slits are disposed on a reverse side of the semi-rigid sheet, or (ii) an inverted configuration in which at least one of the plurality of locking slits is disposed in an edge region of the semi-rigid sheet and at least one of the plurality of adjustable tabs is flexible towards the edge region, and at least another one of the plurality of locking slits is disposed in an interior region of the semi-rigid sheet and at least another one of the plurality of adjustable tabs is flexible towards the interior region. The plurality of adjustable tabs and the plurality of locking slits may be disposed on the semi-rigid sheet both in the front and reverse configuration and in the inverted configuration. The plurality of adjustable tabs and the plurality of locking slits may secure multiple ones of the coils of tubing on each side of the semi-rigid sheet. Each of the plurality of adjustable tabs may be flexible and, when bent or rolled, form a loop to hold a coil of tubing on the semi-rigid sheet. Each of the plurality of adjustable tabs may include a shaped end that is flexible and engages with one of the plurality of locking slits to secure the adjustable tab in a loop to hold a coil of tubing on the semi-rigid sheet. The semi-rigid sheet may be a plastic sheet, each of the shaped ends of the plurality of adjustable tabs may have a rectangular shape, and each of the plurality of locking slits may include fillets that receive and secure edges of the rectangular shaped ends of the adjustable tabs.

According further to the system described herein, a dialysis system includes a dialysis machine having medical tubing and a tube holding device that holds the medical tubing. The tube holding device includes a semi-rigid sheet, a plurality of adjustable tabs disposed on the semi-rigid sheet, and a plurality of locking slits that receive the plurality of adjustable tabs to secure coils of medical tubing to the plastic sheet. The plurality of adjustable tabs and the plurality of locking slits are disposed on the semi-rigid sheet in at least one of: (i) a front and reverse configuration in which at least one of the plurality of adjustable tabs and at least one of the plurality of locking slits are disposed on a front side of the semi-rigid sheet, and at least another one of the plurality of adjustable tabs and at least another one of the plurality of locking slits are disposed on a reverse side of the semi-rigid sheet, or (ii) an inverted configuration in which at least one of the plurality of locking slits is disposed in an edge region of the semi-rigid sheet and at least one of the plurality of adjustable tabs is flexible towards the edge region, and at least another one of the plurality of locking slits is disposed in an interior region of the semi-rigid sheet and at least another one of the plurality of adjustable tabs is flexible towards the interior region. The plurality of adjustable tabs and the plurality of locking slits may be disposed on the semi-rigid sheet both in the front and reverse configuration and in the inverted configuration. The plurality of adjustable tabs and the plurality of locking slits may secure multiple ones of the coils of tubing on each side of the semi-rigid sheet. Each of the plurality of adjustable tabs may be flexible and, when bent or rolled, form a loop to hold a coil of tubing on the semi-rigid sheet. Each of the plurality of adjustable tabs may include a shaped end that is flexible and engages with one of the plurality of locking slits to secure the adjustable tab in a loop to hold a coil of tubing on the semi-rigid sheet. The semi-rigid sheet may be a plastic sheet, each of the shaped ends of the plurality of adjustable tabs may have a rectangular shape, and each of the plurality of locking slits may include fillets that receive and secure edges of the rectangular shaped ends of the adjustable tabs. The dialysis machine may be a peritoneal dialysis machine or a hemodialysis machine.

According further to the system described herein, a method for holding medical tubing providing a semi-rigid sheet, providing a plurality of adjustable tabs disposed on the semi-rigid sheet, and providing a plurality of locking slits that receive the plurality of adjustable tabs to secure coils of medical tubing to the plastic sheet. The plurality of adjustable tabs and the plurality of locking slits are disposed on the semi-rigid sheet in at least one of: (i) a front and reverse configuration in which at least one of the plurality of adjustable tabs and at least one of the plurality of locking slits are disposed on a front side of the semi-rigid sheet, and at least another one of the plurality of adjustable tabs and at least another one of the plurality of locking slits are disposed on a reverse side of the semi-rigid sheet, or (ii) an inverted configuration in which at least one of the plurality of locking slits is disposed in an edge region of the semi-rigid sheet and at least one of the plurality of adjustable tabs is flexible towards the edge region, and at least another one of the plurality of locking slits is disposed in an interior region of the semi-rigid sheet and at least another one of the plurality of adjustable tabs is flexible towards the interior region. The method further includes engaging each of the plurality of adjustable tabs into counterpart ones of the locking slits to form loops to hold the medical tubing on the semi-rigid sheet. The plurality of adjustable tabs and the plurality of locking slits may be disposed on the semi-rigid sheet both in the front and reverse configuration and in the inverted configuration. The plurality of adjustable tabs and the plurality of locking slits may secure multiple ones of the coils of tubing on each side of the semi-rigid sheet. Each of the plurality of adjustable tabs may be flexible and, when bent or rolled, form a loop to hold a coil of tubing on the semi-rigid sheet. Each of the plurality of adjustable tabs may include a shaped end that is flexible and engages with one of the plurality of locking slits to secure the adjustable tab in a loop to hold a coil of tubing on the semi-rigid sheet. The semi-rigid sheet may be a plastic sheet, each of the shaped ends of the plurality of adjustable tabs may have a rectangular shape, and each of the plurality of locking slits may include fillets that receive and secure edges of the rectangular shaped ends of the adjustable tabs.

BRIEF DESCRIPTION OF THE DRAWINGS

Embodiments and features of the system described herein are explained with reference to the several figures of the drawings, which are briefly described as follows.

DETAILED DESCRIPTION OF VARIOUS EMBODIMENTS

Figure 1:
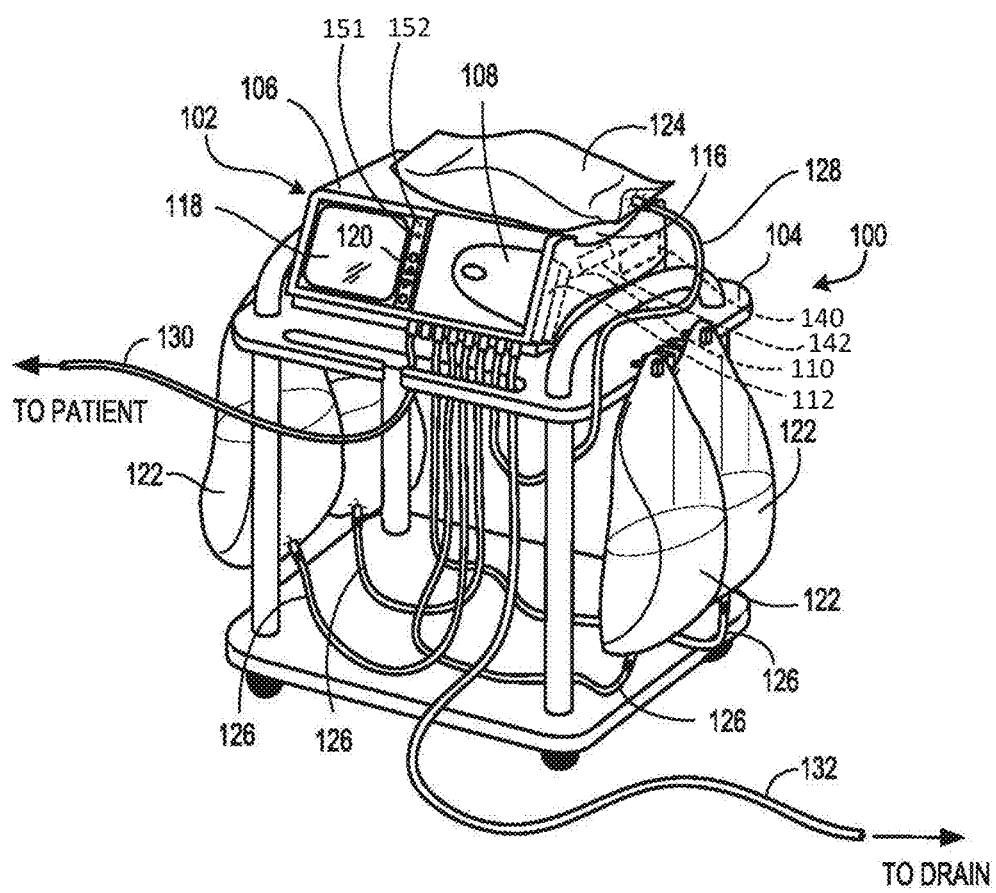
FIG. 1 shows a schematic illustration of a dialysis system having tubing and other components that may be packaged, organized and/or used in connection with an embodiment of the system described herein.

FIG. 1 shows a schematic illustration of a dialysis system having tubing and other components that may be packaged, organized and/or used in connection with an embodiment of the system described herein. The dialysis system may be a peritoneal dialysis (PD) system 100 that includes a PD machine or cycler 102 seated on a cart 104. Although a PD system is principally discussed herein, it is noted that the system described herein may be used in connection with other types of medical devices and/or dialysis systems having medical tubing or lines. For example, the system described herein may be used in connection with a hemodialysis (HD) system.

The PD machine 102 includes a housing 106, a door 108, and a cassette interface 110 that contacts a disposable PD cassette 112 when the cassette 112 is disposed within a cassette compartment formed between the cassette interface 110 and the closed door 108. A heater tray 116 is positioned on top of the housing 106. The heater tray 116 is sized and shaped to accommodate a bag of dialysate (e.g. a 5 liter bag of dialysate). The PD machine 102 also includes a user interface such as a touch screen display 118 and additional control buttons 120 that can be operated by a user (e.g. a caregiver or a patient) to allow, for example, set up, initiation, and/or termination of a PD treatment.

Dialysate bags 122 are suspended from support fingers on the sides of the cart 104, and a heater bag 124 is positioned in the heater tray 116. The dialysate bags 122 and the heater bag 124 are connected to the cassette 112 via dialysate bag lines 126 and a heater bag line 128, respectively. The dialysate bag lines 126 can be used to pass dialysate from dialysate bags 122 to the cassette 112 during use, and the heater bag line 128 can be used to pass dialysate back and forth between the cassette 112 and the heater bag 124 during use. In addition, a patient line 130 and a drain line 132 are connected to the cassette 112. The patient line 130 can be connected to a patient's abdomen via a catheter and can be used to pass dialysate back and forth between the cassette 112 and the patient's peritoneal cavity during use. The drain line 132 can be connected to a drain or drain receptacle and can be used to pass dialysate from the cassette 112 to the drain or drain receptacle during use. As further discussed elsewhere herein, one or more of the lines 126, 128, 130, 132 may be packaged, organized and/or facilitated using an embodiment of the system described herein.

The PD machine 102 includes a control unit 140 (e.g. a processor) and one or more interface components or sensors, such as a microphone/speaker assembly 151 and/or a motion sensor 152 that detects motion of a nearby user. The control unit 140 can receive signals from and transmit signals to the touch screen display 118, the control panel 120, the microphone/speaker assembly, the motion sensor 152, and/or various other components of the PD system 100.

The PD machine 102 may also include a data storage and/or transmission component 142 that may be coupled to the control unit 140 and that may enable the storage of data on the PD machine and/or the transmission of data to and from the PD machine 102. In various implementations, the data may include prescription information, treatment data and/or other therapy-based data and/or may include authorization information and/or other user profile-based information. In various implementations, the component 142 may include a wired connection to a network/Internet, an interface for receiving a physical storage unit, such as a universal serial bus (USB) memory unit, that may be used to transfer and receive data and/or wireless transmission components for transmitting or receiving data and/or other signals wirelessly. The wireless transmission components may include components for short range wireless transmission technologies, such as Bluetooth and/or near field communications (NFC) technologies, for communication with one or more peripheral devices and/or network transmission component. The communication may include transmitting and receiving data and/or other signals wirelessly via a telecommunications network and/or the Internet to/from one or more remote servers. In connection with transmission, data may be secured and/or encrypted via the control unit 140 using appropriate security and encryption protocols according to applicable laws and regulations governing transmission of sensitive data and/or protected medical information.

A device and method for holding coils of medical tubing is provided according to the system described herein to simplify packaging and organizing the various coils of medical tubing needed for a medical device. This will make it easier for the patient to manipulate each coil of tubing, particularly in a home setting involving a home dialysis machine operated by the patient. The tube holding device advantageously reduces the probability of entanglement and groups the coils of tubing individually. It also mitigates and/or eliminates the need for tape to bundle the coils. Specifically, benefits of the tube holding device according to the system described herein include: reduced cost; ease-of-use; prevention of entanglement of coils of tubing; ease of packaging and shipping; and does not require packaging tape to bundle tubing.

Figure 2:
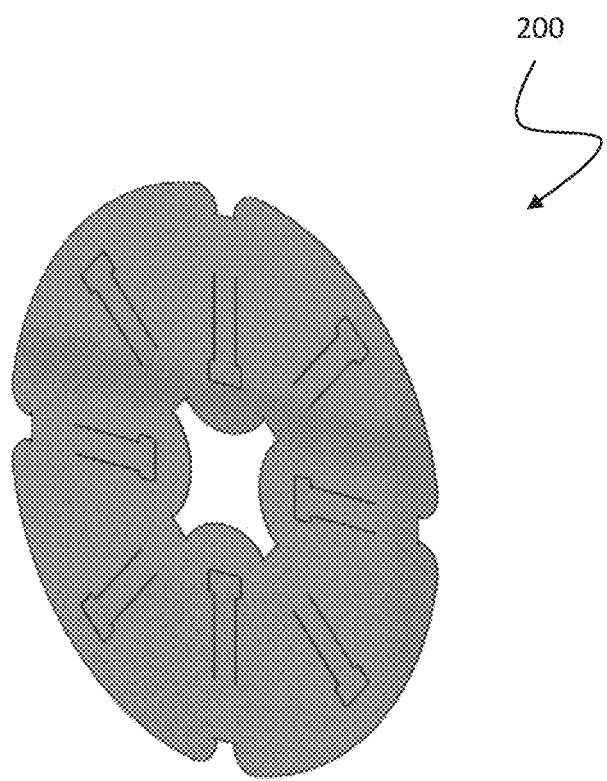
FIG. 2 is a schematic illustration of a tube holding device according to an embodiment of the system described herein.

FIG. 2 is a schematic illustration of a tube holding device 200 according to an embodiment of the system described herein. A flat pattern of the device 200 may be cut from a sheet of flexible material that has some rigidity (semi-rigid), such as a plastic sheet, e.g. a 0.015 inch-thick Mylar® sheet. Although a plastic sheet is principally discussed herein, suitable materials other than plastic may also be used having the structure and serving the functions discussed herein. The flat pattern includes adjustable tabs having shaped ends. The ends are shown in the figure as rectangular, although others shapes may be used in connection with the system described herein in accordance with an interlocking design with locking slits on the tube holding device 200. As discussed in further detail elsewhere herein, the rectangular ends may be folded and the adjustable tabs are flexible and may be bent or rolled in directions substantially perpendicular to one or more of the planar faces of the plastic sheet of the tube holding device 200.

The tube holding device 200 may include a front and reverse configuration in which the interlocking design may be reversible to include locking slits and adjustable tabs on each face of the plastic sheet to hold coils of tubing on each side (front and reverse) of the tube holding device 200. The tube holding device 200 may also include an inverted configuration in which some of the adjustable tabs are designed to be bent or rolled and locked into locking slits disposed on the edge of the plastic sheet while other of the adjustable tabs are designed to be bent or rolled and locked into locking slits disposed on an interior portion of the plastic sheet, such as in a cut-out from the interior of the plastic sheet, as shown in the figure. The use of the adjustable tabs and locking slits, as discussed in detail herein, advantageously avoids the need for tape or glue to hold the medical tubing on the plastic sheet.

Figure 3:
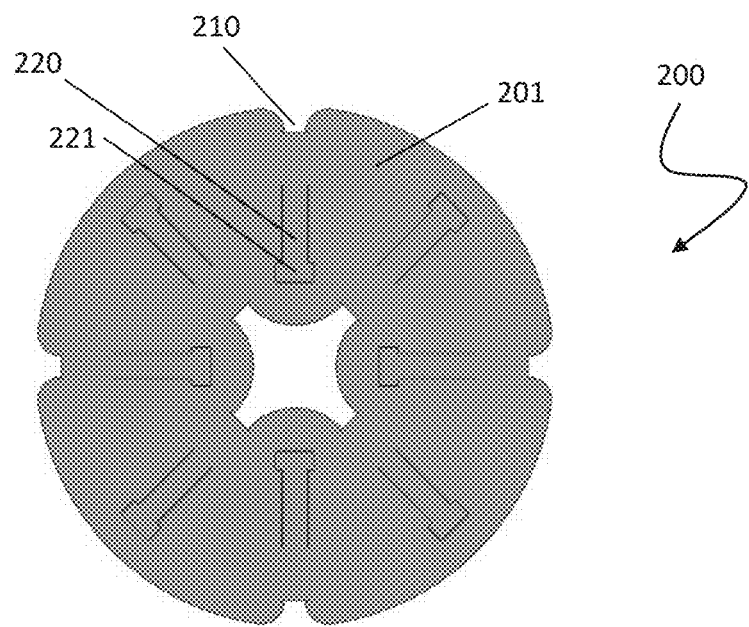
FIG. 3 is a schematic illustration showing a front view of the tube holding device having a plastic sheet according to an embodiment of the system described herein.

FIG. 3 is a schematic illustration showing a front view of tube holding device 200 showing the plastic sheet 201 after it has been die cut according to an embodiment of the system described herein. A locking slit 210 is shown which allows the adjustable tab 220 having a rectangular end 221 to lock into place in the locking slit 210. Other slits and tabs shown on the device may be similarly configured.

Figure 4:
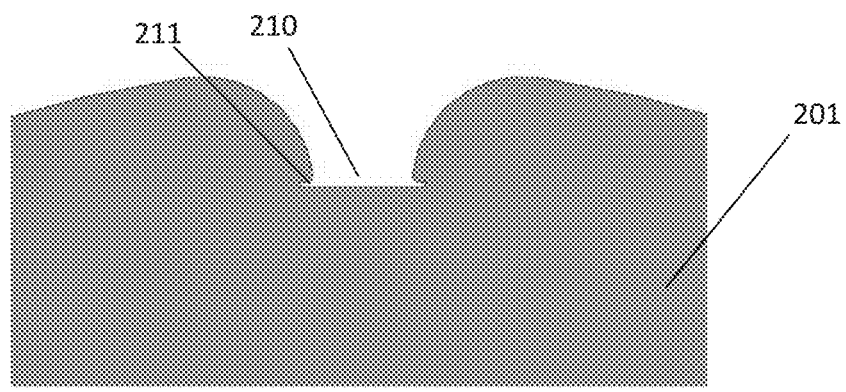
FIG. 4 is a detailed schematic view of a locking slit and in which is shown that fillets on one or more sides of the locking slit allow the adjustable tab to be guided into the locking slit and held in place on the plastic sheet according to an embodiment of the system described herein.

FIG. 4 is a detailed schematic view of the locking slit 210 and in which is shown that fillets 211 on one or more sides of the locking slit 210 allow the adjustable tab 220 to be easily guided into the locking slit 210 and held in place on the plastic sheet 201 according to an embodiment of the system described herein.

Figure 5:
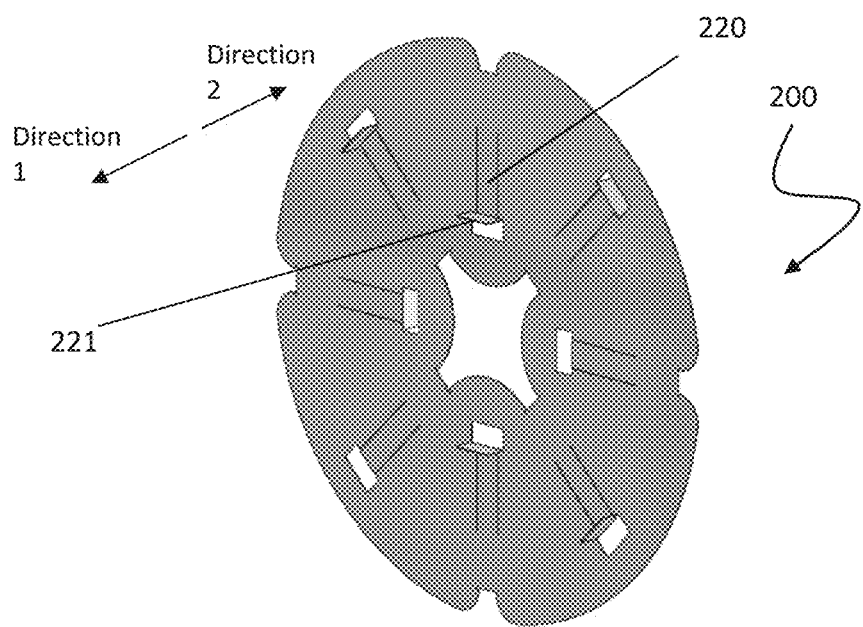
FIG. 5 is a schematic illustration showing a configuration of the tube holding device in which the rectangular end of each adjustable tab may be folded according to an embodiment of the system described herein.

FIG. 5 is a schematic illustration showing a configuration of the tube holding device 200 in which the rectangular end 221 of each adjustable tab 220 may be folded according to an embodiment of the system described herein. Some of the rectangular ends are shown folded in direction 1, and other of the rectangular ends are shown folded in direction 2 that is shown as parallel but opposite to direction 1 in connection with the front and reverse configuration of the tube holding device 200 that may be configured to hold multiple coils of tubes on each side (front and reverse) of the plastic sheet 201.

Figure 6:
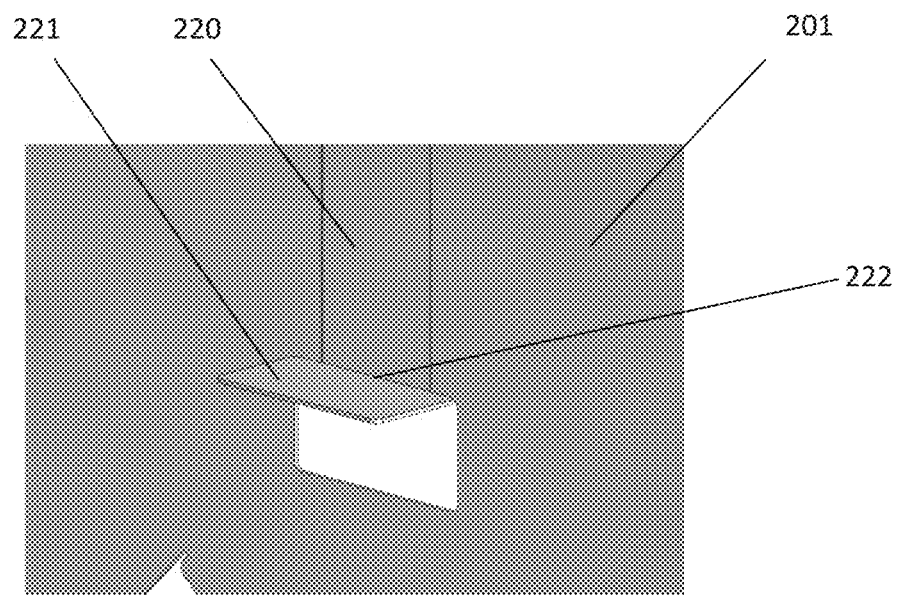
FIG. 6 is a schematic illustration showing an expanded view of the rectangular end of the adjustable tab having a perforated edge line to make it easier to fold according to an embodiment of the system described herein.

FIG. 6 is a schematic illustration showing an expanded view of the rectangular end 221 of the adjustable tab 220 having a perforated edge line 222 to make it easier to fold according to an embodiment of the system described herein. The folded rectangular end 221 may be used to secure the adjustable tab 220, after it has been bent or rolled around a coil of tubing and into a loop over the plastic sheet 201 and thereby secure the tubing to the plastic sheet 201. The rectangular end 221 is fitted over the locking slit 210 and folded against the plastic sheet 201 to secure the adjustable tab 220 in place.

Figure 7:
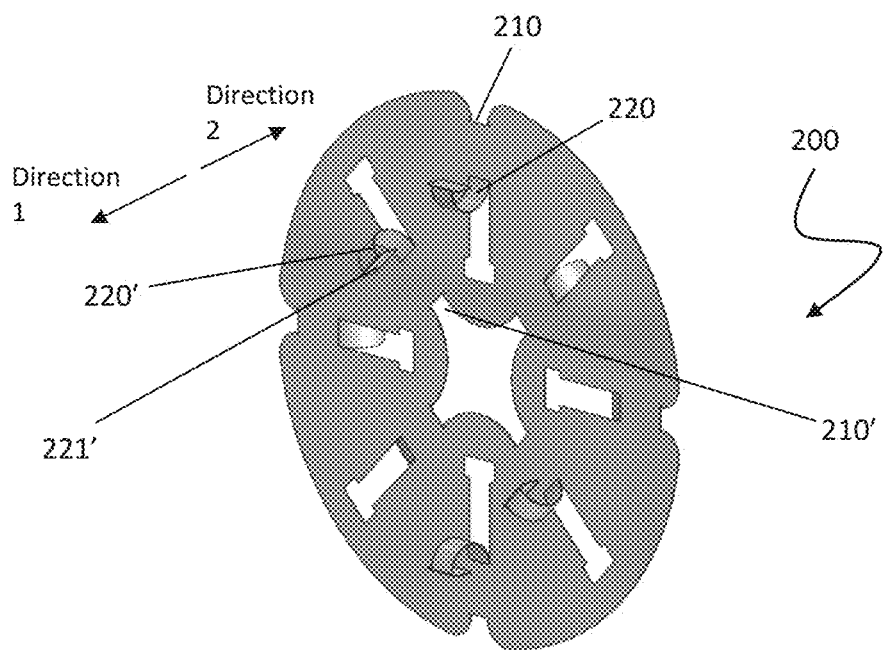
FIG. 7 is a schematic illustration showing some of the adjustable tabs of the tube holding device that are bent or rolled in direction 1 and other of the adjustable tabs that are bent or rolled in direction 2 according to an embodiment of the system described herein.

FIG. 7 is a schematic illustration showing some of the adjustable tabs (e.g. adjustable tabs 220, 220') of the tube holding device 200 that are bent or rolled in direction 1 and other of the adjustable tabs (e.g. adjustable tab 220"—see below) that are bent or rolled in direction 2 according to an embodiment of the system described herein. The adjustable tabs 220, 220' shown bent or rolled in direction 1 are shown in the inverted configuration in which adjustable tab 200 is rolled towards the outer edge of the plastic sheet 201 whereas the adjustable tab 220' is rolled towards the interior region of the plastic sheet 201, specifically towards a cut-out portion of the interior region. Each of the adjustable tabs 220, 220' may be inserted into locking slits (e.g. locking slits 210, 210') and include foldable rectangular ends (e.g. rectangular ends 221, 221') that help secure the adjustable tabs to the plastic sheet 201. Locking slit 210 is shown disposed on the outer edge of the plastic sheet 201 whereas locking slit 210' is shown disposed in the interior of the plastic sheet 201, specifically on the cut-out portion of the interior region of the plastic sheet 201.

Figure 8:
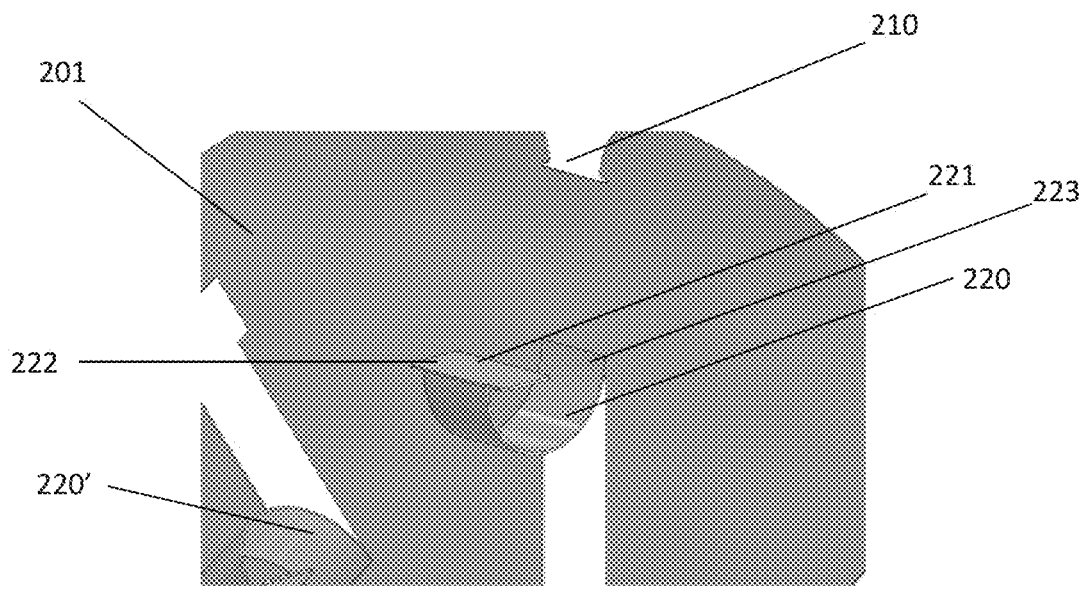
FIG. 8 is a schematic illustration showing an expanded view of an adjustable tab having a perforated edge line to make it easier to bend in the desired direction and one which the rectangular end is shown folded along edge line according to an embodiment of the system described herein.

FIG. 8 is a schematic illustration showing an expanded view of an adjustable tab 220 having a perforated edge line 223 to make it easier to bend in the desired direction and one which the rectangular end 221 is shown folded along edge line 222 according to an embodiment of the system described herein. To secure tubing to the plastic sheet 201, the adjustable tab 220 is inserted into the locking slit 221 and held in place by the rectangular end 223 folded onto the reverse side of the plastic sheet 201. Similar action may be performed using other adjustable tabs (e.g. adjustable tab 220') on the tube holding device 200.

Figure 9:
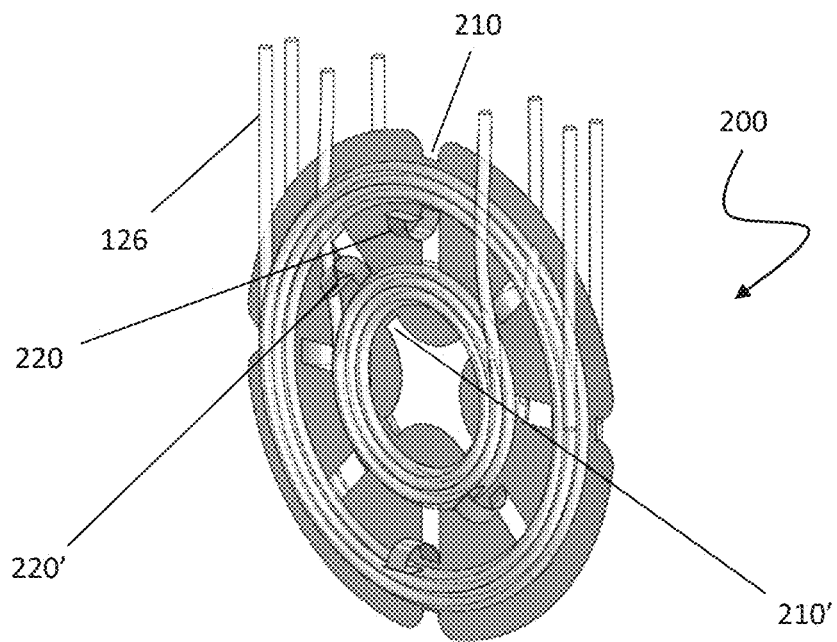
FIG. 9 is a schematic illustration showing coils of tubing that are placed and aligned on each side of the tube holding device, with two coils of tubing on each side according to an embodiment of the system described herein.

FIG. 9 is a schematic illustration showing coils of tubing 126 that are placed and aligned on each side of the tube holding device 200, with two coils of tubing on each side according to an embodiment of the system described herein, in preparation for being secured to the tube holding device 200 using the adjustable tabs (e.g. adjustable tabs 220, 220', 220") with rectangular ends (e.g. rectangular end 221, 221', 221") that are inserted into locking slits (e.g. locking slits 210, 210', 210").

Figure 10:
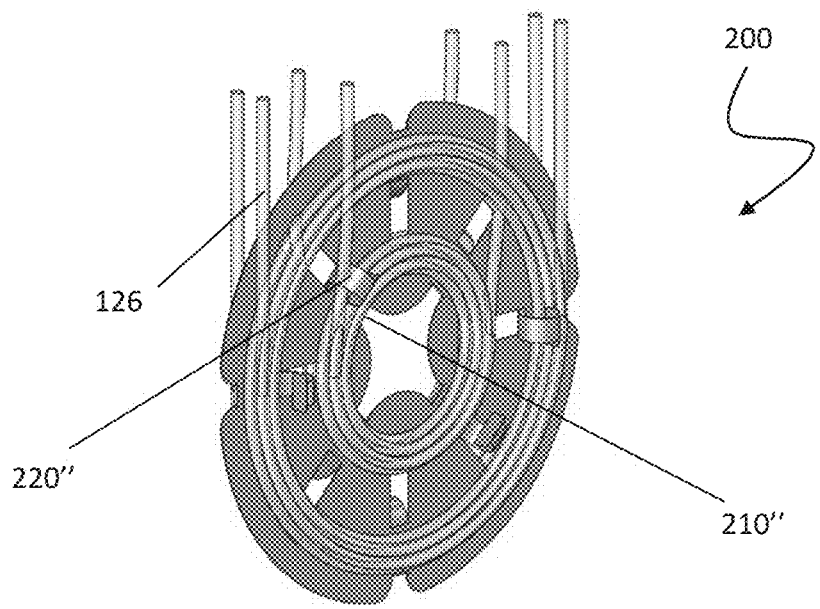
FIG. 10 is a schematic illustration showing a back view of the tube holding device according to an embodiment of the system described herein in which some tabs are shown bent or rolled in the opposite direction from the tabs on the opposite side of the plastic sheet according to an embodiment of the system described herein.

FIG. 10 is a schematic illustration showing a back view of the tube holding device 200 according to an embodiment of the system described herein in which some tabs (e.g. adjustable tab 220") are shown bent or rolled in the opposite direction from the tabs (e.g. adjustable tabs 220, 220') on the opposite side of the plastic sheet 201 according to an embodiment of the system described herein. The adjustable tabs on each side of the plastic sheet 201 secure coils of tubing 126 and exemplify a front and reverse configuration of the tube holding device 200. As shown in the figures, four coils of tubing 126 are shown in the process of being secured and organized by the tube holding device 200, for example, in connection with packaging and/or use of the tubing 126.

Figure 11:
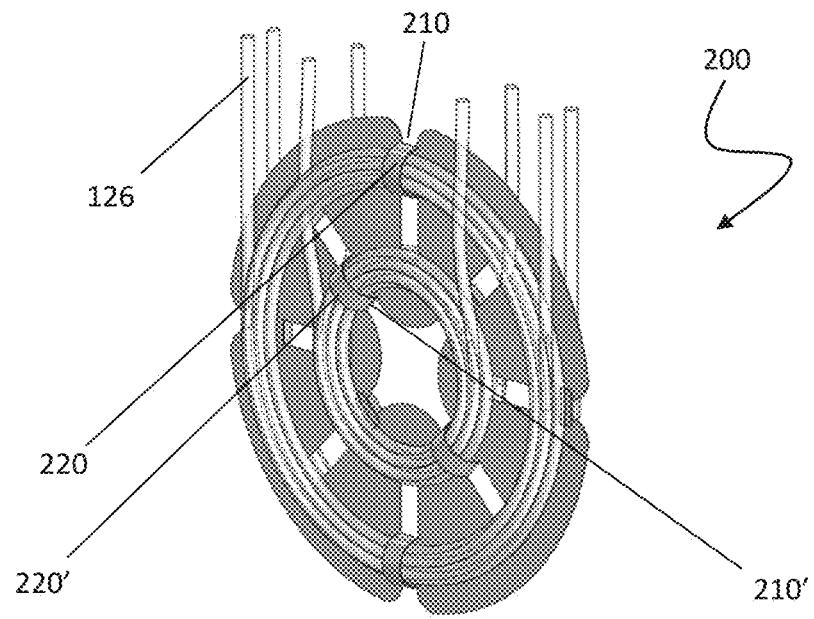
FIG. 11 is a schematic illustration the tube holding device showing that the adjustable tabs are bent or rolled over the tubing and the rectangular ends thereof locked into the locking slits according to an embodiment of the system described herein.

FIG. 11 is a schematic illustration of the tube holding device 200 showing that the adjustable tabs (e.g. adjustable tabs 220, 220') are bent or rolled over the tubing 126 and the rectangular ends thereof locked into the locking slits (e.g. locking slits 210, 210') according to an embodiment of the system described herein. The tubing 126 is thereby secured and held onto the plastic sheet 201 of the tube holding device 200.

Figure 12:
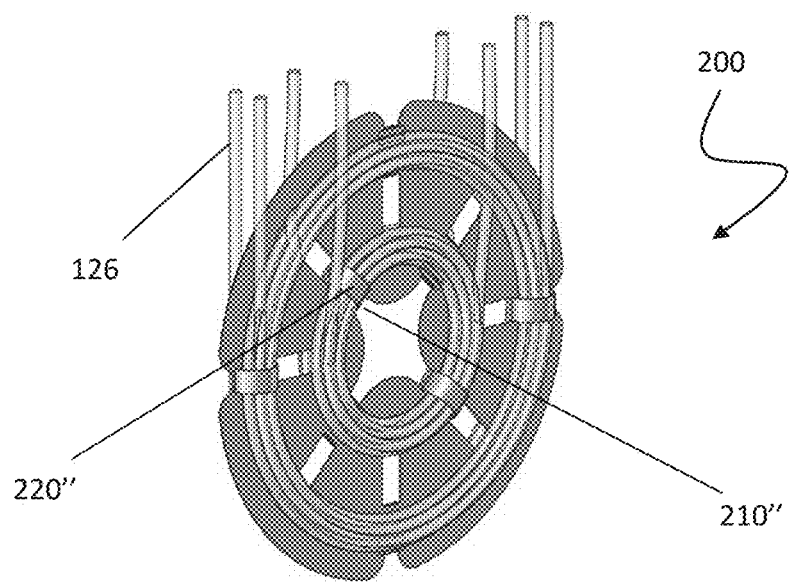
FIG. 12 is a schematic illustration showing a back view of the tube holding device and on which the coils of tubing on the reverse side of the plastic sheet of the tube holding device are secured by the adjustable tabs inserted into a locking slit according to an embodiment of the system described herein.

FIG. 12 is a schematic illustration showing a back view of the tube holding device 200 and on which the coils of tubing 126 on the reverse side of the plastic sheet 201 of the tube holding device 200 are secured by the adjustable tabs (e.g. adjustable tab 220") inserted into locking slits (e.g. locking slit 210") according to an embodiment of the system described herein. As shown, the locking slit 210" is disposed on an interior portion of the plastic sheet 201 and the adjustable tab 220" is bent or rolled towards the center of the plastic sheet 201 and secured in the locking slit 210". Additional locking slits are shown on the reverse side of the plastic sheet 201, including locking slits disposed on the edge region of the plastic sheet 201 and the interior region of the plastic sheet 201 on an interior cut-out thereof.

Figure 13:
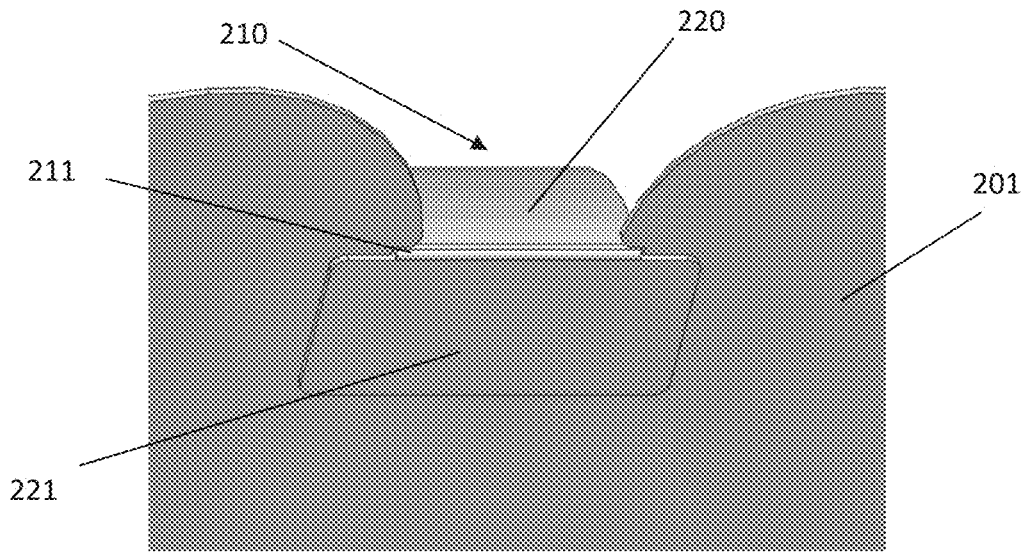
FIG. 13 is a enlarged view of an adjustable tab inserted in the locking slit and on which a rectangular end of the adjustable tab secures the adjustable tab to the plastic sheet of the tub holding device according to an embodiment of the system described herein.

FIG. 13 is an enlarged schematic view of the adjustable tab 220 after insertion into the locking slit 210 in connection with securing tubing on the tube holding device 200. Note that the rectangular end 221 of the adjustable tab 220 is folded over and becomes almost parallel with the plastic sheet 201 of the tube holding device 200 thereby securing the adjustable tab 220 in place. Also note the adjustable tab 220 is wider than the locking slit 210 and is disposed into the fillets 211 of the locking slit 210 which helps prevent the adjustable tab 220 from sliding out of the locking slit 210. Other adjustable tabs and locking slits on both sides of the plastic sheet 201 may function similarly.

Figure 14:
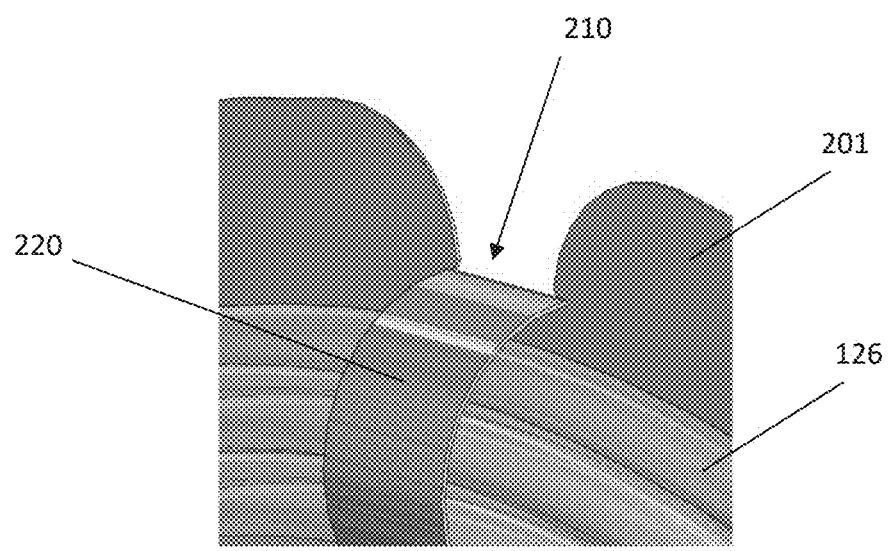
FIG. 14 is an enlarged view of an adjustable tab locked in the locking slit and holding a coil of tubing within the loop according to an embodiment of the system described herein.

FIG. 14 is an enlarged schematic view of the adjustable tab 220 locked in the locking slit 210 and holding a coil of tubing 126 within a loop formed by the adjustable tab 220 above a planar face of the plastic sheet 201 of the tube holding device 200 according to an embodiment of the system described herein. The coil of tubing 126 is thereby secured to the plastic sheet 201 suitably for packaging and/or use.

Figure 15:
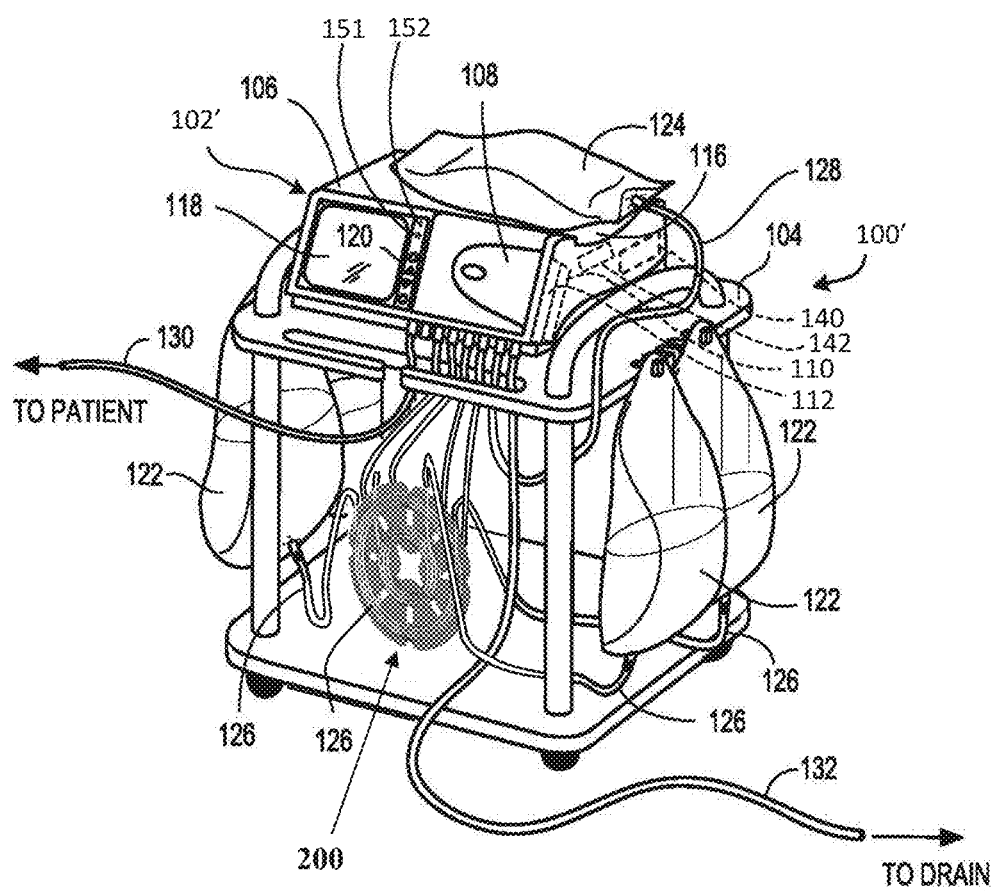
FIG. 15 is a schematic illustration showing a dialysis system including a PD cycler on which is disposed a medical tube holding device holding medical tubing according to an embodiment of the system described herein.

FIG. 15 is a schematic illustration showing a dialysis system 100' including a dialysis machine 102', such as a PD cycler, on which is disposed a tube holding device 200 holding medical tubing 126 according to an embodiment of the system described herein. In various embodiments, the tube holding device 200 may be used to package and organize the tubing 126 of the dialysis machine 102' in connection with shipping and setup of the tubing at the dialysis machine 102'. The tube holding device 200 may then be subsequently removed after the tubing has been setup and organized but prior to operation of the dialysis system 100'. In other embodiments, the tube holding device 200 may be maintained on the dialysis machine 102' during operation such that fluid flows through the tubing while positioned by the tube holding device 200. In other embodiments, the tube holding device 200 may be disposed in a different orientation than that shown and/or may be disposed on a mounting assembly.

Various embodiments discussed herein may be combined with each other in appropriate combinations in connection with the system described herein. Additionally, in some instances, the order of steps in the flow diagrams, flowcharts and/or described flow processing may be modified, where appropriate.

embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A device for holding medical tubing, comprising:
 a semi-rigid sheet having a circular shape with an edge region and an interior region disposed radially inward from the edge region on the semi-rigid sheet;
 a plurality of adjustable tabs disposed on the semi-rigid sheet; and
 a plurality of locking slits that receive the plurality of adjustable tabs in a configuration to secure coils of medical tubing to the semi-rigid sheet, wherein the plurality of adjustable tabs and the plurality of locking slits are disposed on the semi-rigid sheet in:
  (i) a front and reverse configuration in which at least one of the plurality of adjustable tabs and at least one of the plurality of locking slits are disposed on a front side of the semi-rigid sheet, and at least another one of the plurality of adjustable tabs and at least another one of the plurality of locking slits are disposed on a reverse side of the semi-rigid sheet, and
  (ii) an inverted configuration in which at least one of the plurality of locking slits is disposed in the edge region of the semi-rigid sheet and at least one of the plurality of adjustable tabs is flexible towards the edge region, and at least another one of the plurality of locking slits is disposed in the interior region of the semi-rigid sheet and at least another one of the plurality of adjustable tabs is flexible towards the interior region,
 wherein each side of the semi-rigid sheet is configured to hold at least two coils of tubing, including a first coil of tubing at the edge region and a second coil of tubing at the interior region radially within the first coil of tubing, using the plurality of adjustable tabs and locking slits in the front and reverse configuration and the plurality of adjustable tabs and the plurality of locking slits in the inverted configuration.

2. The device according to claim 1, wherein each of the plurality of adjustable tabs is flexible and, when bent or rolled, forms a loop to hold a coil of tubing on the semi-rigid sheet.

3. The device according to claim 1, wherein each of the plurality of adjustable tabs includes a shaped end that is flexible and engages with one of the plurality of locking slits to secure the adjustable tab in a loop to hold a coil of tubing on the semi-rigid sheet.

4. The device according to claim 3, wherein the semi-rigid sheet is a plastic sheet, each of the shaped ends of the plurality of adjustable tabs has a rectangular shape, and each of the plurality of locking slits includes fillets that receive and secure edges of the rectangular shaped ends of the adjustable tabs.

5. A dialysis system, comprising:
 a dialysis machine having medical tubing; and
 a tube holding device that holds the medical tubing, wherein the tube holding device comprises:
  a semi-rigid sheet having a circular shape with an edge region and an interior region disposed radially inward from the edge region on the semi-rigid sheet;
  a plurality of adjustable tabs disposed on the semi-rigid sheet;
  a plurality of locking slits that receive the plurality of adjustable tabs in a configuration to secure coils of the medical tubing to the semi-rigid sheet, wherein the plurality of adjustable tabs and the plurality of locking slits are disposed on the semi-rigid sheet in:
   (i) a front and reverse configuration in which at least one of the plurality of adjustable tabs and at least one of the plurality of locking slits are disposed on a front side of the semi-rigid sheet, and at least another one of the plurality of adjustable tabs and at least another one of the plurality of locking slits are disposed on a reverse side of the semi-rigid sheet, and
   (ii) an inverted configuration in which at least one of the plurality of locking slits is disposed in the edge region of the semi-rigid sheet and at least one of the plurality of adjustable tabs is flexible towards the edge region, and at least another one of the plurality of locking slits is disposed in the interior region of the semi-rigid sheet and at least another one of the plurality of adjustable tabs is flexible towards the interior region,
 wherein each side of the semi-rigid sheet is configured to hold at least two coils of tubing, including a first coil of tubing at the edge region and a second coil of tubing at the interior region radially within the first coil of tubing, using the plurality of adjustable tabs and locking slits in the front and reverse configuration and the plurality of adjustable tabs and the plurality of locking slits in the inverted configuration.

6. The dialysis system according to claim 5, wherein each of the plurality of adjustable tabs is flexible and, when bent or rolled, forms a loop to hold a coil of tubing on the semi-rigid sheet.

7. The dialysis system according to claim 5, wherein each of the plurality of adjustable tabs includes a shaped end that is flexible and engages with one of the plurality of locking slits to secure the adjustable tab in a loop to hold a coil of tubing on the semi-rigid sheet.

8. The dialysis system according to claim 7, wherein the semi-rigid sheet is a plastic sheet, each of the shaped ends of the plurality of adjustable tabs has a rectangular shape, and each of the plurality of locking slits includes fillets that receive and secure edges of the rectangular shaped ends of the adjustable tabs.

9. The dialysis system according to claim 5, wherein the dialysis machine is a peritoneal dialysis machine.

10. The dialysis system according to claim 5, wherein the dialysis machine is a hemodialysis machine.

11. A method for holding medical tubing, comprising:
providing a semi-rigid sheet having a circular shape with an edge region and an interior region disposed radially inward from the edge region on the semi-rigid sheet;
providing a plurality of adjustable tabs disposed on the semi-rigid sheet;
providing a plurality of locking slits that receive the plurality of adjustable tabs in a configuration to secure coils of medical tubing to the plastic sheet, wherein the plurality of adjustable tabs and the plurality of locking slits are disposed on the semi-rigid sheet in:
  (i) a front and reverse configuration in which at least one of the plurality of adjustable tabs and at least one of the plurality of locking slits are disposed on a front side of the semi-rigid sheet, and at least another one of the plurality of adjustable tabs and at least another one of the plurality of locking slits are disposed on a reverse side of the semi-rigid sheet, and
  (ii) an inverted configuration in which at least one of the plurality of locking slits is disposed in the edge region of the semi-rigid sheet and at least one of the plurality of adjustable tabs is flexible towards the edge region, and at least another one of the plurality of locking slits is disposed in the interior region of the semi-rigid sheet and at least another one of the plurality of adjustable tabs is flexible towards the interior region,
wherein each side of the semi-rigid sheet is configured to hold at least two coils of tubing, including a first coil of tubing at the edge region and a second coil of tubing at the interior region radially within the first coil of tubing, using the plurality of adjustable tabs and locking slits in the front and reverse configuration and the plurality of adjustable tabs and the plurality of locking slits in the inverted configuration; and
engaging each of the plurality of adjustable tabs into counterpart ones of the locking slits to form loops to hold the medical tubing on the semi-rigid sheet.

12. The method according to claim 11, wherein each of the plurality of adjustable tabs is flexible and, when bent or rolled, forms a loop to hold a coil of tubing on the semi-rigid sheet.

13. The method according to claim 11, wherein each of the plurality of adjustable tabs includes a shaped end that is flexible and engages with one of the plurality of locking slits to secure the adjustable tab in a loop to hold a coil of tubing on the semi-rigid sheet.

14. The method according to claim 13, wherein the semi-rigid sheet is a plastic sheet, each of the shaped ends of the plurality of adjustable tabs has a rectangular shape, and each of the plurality of locking slits includes fillets that receive and secure edges of the rectangular shaped ends of the adjustable tabs.

* * * * *